US010282517B2

(12) United States Patent
Miura

(10) Patent No.: US 10,282,517 B2
(45) Date of Patent: May 7, 2019

(54) APPARATUS, METHOD, AND NON-TRANSITORY COMPUTER-READABLE MEDIUM FOR SUPPORTING VIEWING EXAMINATION IMAGES

(71) Applicant: FUJIFILM Corporation, Tokyo (JP)

(72) Inventor: Nobuyuki Miura, Tokyo (JP)

(73) Assignee: FUJIFILM Corporation, Minato-Ku, Tokyo (JP)

( * ) Notice: Subject to any disclaimer, the term of this patent is extended or adjusted under 35 U.S.C. 154(b) by 483 days.

(21) Appl. No.: 15/083,887

(22) Filed: Mar. 29, 2016

(65) Prior Publication Data
US 2016/0287053 A1 Oct. 6, 2016

(30) Foreign Application Priority Data

Mar. 30, 2015 (JP) ................................. 2015-070157

(51) Int. Cl.
G06K 9/00 (2006.01)
A61B 8/14 (2006.01)
G06F 19/00 (2018.01)

(52) U.S. Cl.
CPC ............ G06F 19/321 (2013.01); G06F 19/00 (2013.01)

(58) Field of Classification Search
USPC ....... 382/100, 103, 106, 128–133, 168, 173, 382/181, 189, 219, 232, 254, 276, 382/286–291, 305; 600/407, 462; 348/65; 705/2; 715/764
See application file for complete search history.

(56) References Cited

U.S. PATENT DOCUMENTS

| 2005/0177394 | A1* | 8/2005 | Hosoya ................. G16H 15/00 705/2 |
| 2009/0019381 | A1* | 1/2009 | Kimoto ............. A61B 1/00009 715/764 |
| 2009/0054755 | A1* | 2/2009 | Shiibashi ............. G06F 19/321 600/407 |
| 2010/0067808 | A1 | 3/2010 | Matsuzaki |
| 2010/0115469 | A1 | 5/2010 | Shigemori |

(Continued)

FOREIGN PATENT DOCUMENTS

JP 2005-160661 A 6/2005
JP 2007-075155 A 3/2007

(Continued)

OTHER PUBLICATIONS

Communication drafted Feb. 16, 2018, from the Japanese Patent Office in counterpart application No. 2015-070157.

Primary Examiner — Seyed H Azarian
(74) Attorney, Agent, or Firm — Sughrue Mion, PLLC

(57) ABSTRACT

Based on an examination report of an endoscopic examination designated, an attached image extraction unit reads image identification information, which identifies an examination image attached to the examination report. Based on the image identification information, the attached image extraction unit extracts the examination image (that is, an attached image) attached to the examination report, from examination images corresponding to the designated endoscopic examination. The examination images are read from an image folder of an image database (DB). A screen display controller performs control to display the extracted attached image on a display screen.

10 Claims, 11 Drawing Sheets

(56) References Cited

U.S. PATENT DOCUMENTS

2011/0075901 A1* 3/2011 Nakamura ............ G06F 19/321
                                                        382/128
2014/0063215 A1* 3/2014 Miura .................. A61B 1/0002
                                                        348/65

FOREIGN PATENT DOCUMENTS

| JP | 2007-236726 A | 9/2007 |
| JP | 2008-295490 A | 12/2008 |
| JP | 5147308 B2 | 2/2013 |
| JP | 2014-053723 A | 3/2014 |

* cited by examiner

APPARATUS, METHOD, AND NON-TRANSITORY COMPUTER-READABLE MEDIUM FOR SUPPORTING VIEWING EXAMINATION IMAGES

CROSS-REFERENCE TO RELATED APPLICATIONS

The present application claims priority under 35 U.S.C. § 119 to Japanese Patent Application No. 2015-070157, filed Mar. 30, 2015. Each of the above applications is hereby expressly incorporated by reference, in its entirety, into the present application.

BACKGROUND OF THE INVENTION

1. Field of the invention

The present invention relates to an apparatus, a method, and a non-transitory computer-readable medium for supporting viewing examination images obtained in at least one endoscopic examination.

2. Description Related to the Prior Art

Endoscopes for capturing images of a patient's body cavity are known. An insertion section of the endoscope is inserted into the patient's body cavity and the images are captured by an imaging unit, which is incorporated in a distal end portion of the insertion section. In an endoscopic examination using the endoscope, for example, in a screening examination of an upper gastrointestinal tract, a plurality of still images are captured throughout the upper intestinal tract including mouth, esophagus, and stomach. The number of the still images captured in one screening examination is enormous. For example, in a case where the still images are automatically captured at predetermined time intervals (for example, at time intervals of three seconds), several hundreds of examination images are obtained in one screening examination. These images are stored on a per endoscopic examination basis in a data storage unit (image storage unit) such as an image database.

After the endoscopic examination, a series of the examination images obtained in the endoscopic examination are displayed by an image viewer for viewing the examination images. A doctor views the displayed examination images to perform a diagnosis. The examination images obtained in the endoscopic examination include many images that are unnecessary for the diagnosis. For example, the examination images include those captured in test image capture performed before the endoscopic examination and those automatically captured. In the screening examination, the enormous number of examination images including the unnecessary images are viewed to inspect the presence or absence of abnormalities such as a lesion.

Techniques described in US2010/0067808 (corresponding to Japanese Patent No. 5147308) and US2010/0115469 (corresponding to Japanese Patent Laid-Open Publication No. 2008-295490), which enable quickly viewing the examination images that are necessary for diagnosis, are known.

In the US2010/0067808, the examination image is analyzed and an imaged body part (the esophagus, the stomach, or the like) in the examination image is identified. Some of the examination images having the same body part as the identified body part are extracted and only the extracted examination images are viewed. Thereby the number of the examination images to be viewed is reduced and thus the efficiency in viewing the examination images is improved.

The US2010/0115469 describes a technique to narrow down the examination images by setting a keyword (e.g. an imaged body part), which represents a feature of the examination image, for each examination image. Thereby the examination images to be viewed are narrowed down based on the keyword and thus the efficiency in viewing the examination images is improved.

However, because some of the examination images are extracted through the image analysis in the US2010/0067808, the examination images that are unnecessary for diagnosis may be extracted or the examination images that are necessary for diagnosis may be omitted.

With the use of the technique described in the US2010/0115469, the keyword may be set for each examination image, for example, at the time of the screening examination or at the time of preparation of an examination report, into which a doctor writes findings of the examination image. Subsequently, the examination images that are necessary for diagnosis are viewed easily and quickly by a keyword search.

However, setting the keyword for each examination image needs much time and effort. In particular, for example, in the case of the screening examination, setting the keywords to the enormous number of images requires extreme time and effort.

SUMMARY OF THE INVENTION

An object of the present invention is to provide an apparatus, a method, and a non-transitory computer-readable medium that enable easily and quickly viewing at least one examination image that is significant for diagnosis.

In order to achieve the above and other objects, an aspect of the present invention provides an apparatus for supporting viewing a plurality of examination images comprising an attached image extraction unit and a screen display controller. The attached image extraction unit extracts at least one attached image from the examination images stored in the image storage unit. The attached image is extracted based on an examination report. The examination report is prepared on the per endoscopic examination basis. The at least one of the examination images obtained in the one endoscopic examination is attached to the examination report. The attached image is the examination image attached to the examination report. The screen display controller performs control to display the extracted attached image on a display screen. The examination images are stored on the per endoscopic examination basis in the image storage unit.

It is preferred that the apparatus further comprises an examination designation receiver for receiving designation of the one endoscopic examination from among the endoscopic examinations. It is preferred that the attached image extraction unit extracts the at least one attached image from the examination images obtained in the designated endoscopic examination. It is preferred that the screen display controller displays the at least one attached image, out of the examination images obtained in the designated endoscopic examination, on the display screen.

It is preferred that the examination images include the at least one attached image and at least one unattached image. The unattached image is the examination image not attached to the examination report. It is preferred that the examination images including at least the attached image are displayed in a chronological order of image capture time on the display screen.

It is preferred that the attached image is used as a top image, which is displayed at the top in the chronological order on the display screen, regardless of the image capture time.

It is preferred that, among the attached images, the attached image that is attached as a representative image to the examination report is used as the top image.

It is preferred that the apparatus comprises a first display mode, in which only the attached images are displayed in the chronological order on the display screen, and a second display mode, in which the attached images and the at least one unattached image are displayed in the chronological order on the display screen.

It is preferred that the display screen comprises a switch display area, in which the examination images are selectively displayed one at a time in the chronological order of the image capture time.

It is preferred that the display screen comprises an arrangement display area, in which the examination images arranged in the chronological order of the image capture time are displayed.

It is preferred that the examination images stored on the per endoscopic examination basis include still images that are captured automatically at predetermined time intervals.

An aspect of the present invention provides a method for operating an apparatus for supporting viewing a plurality of examination images. The method comprises an extraction step and a control step. In the extraction step, at least one attached image is extracted from the examination images stored in the image storage unit. The attached image is extracted based on an examination report. The examination report is prepared on the per endoscopic examination basis. The at least one of the examination images obtained in the one endoscopic examination is attached to the examination report. The attached image is the examination image attached to the examination report. In the control step, control is performed to display the extracted attached image on a display screen. The examination images are stored on the per endoscopic examination basis in the image storage unit.

An aspect of the present invention provides a non-transitory computer-readable computer medium having instructions stored therein, which, when executed by a computer, cause the computer to perform operations for supporting viewing a plurality of examination images. The operations comprises an extraction operation and a control operation. In the extraction operation, at least one attached image is extracted from the examination images stored in the image storage unit. The attached image is extracted based on an examination report. The examination report is prepared on the per endoscopic examination basis. The at least one of the examination images obtained in the one endoscopic examination is attached to the examination report. The attached image is the examination image attached to the examination report. In the control operation, control is performed to display the extracted attached image on a display screen. The examination images are stored on the per endoscopic examination basis in an image storage unit.

According to the aspects of the present invention, the at least one attached image, which is attached to the medical report, is extracted and displayed on the display screen. Thereby the at least one examination image that is significant for diagnosis is viewed easily and quickly.

BRIEF DESCRIPTION OF THE DRAWINGS

The above and other objects and advantages of the present invention will be more apparent from the following detailed description of the preferred embodiments when read in connection with the accompanied drawings, wherein like reference numerals designate like or corresponding parts throughout the several views, and wherein:

FIG. 5 is a block diagram illustrating electrical configuration of a computer used as an image view support server apparatus or the like;

DESCRIPTION OF THE PREFERRED EMBODIMENTS

Figure 1:
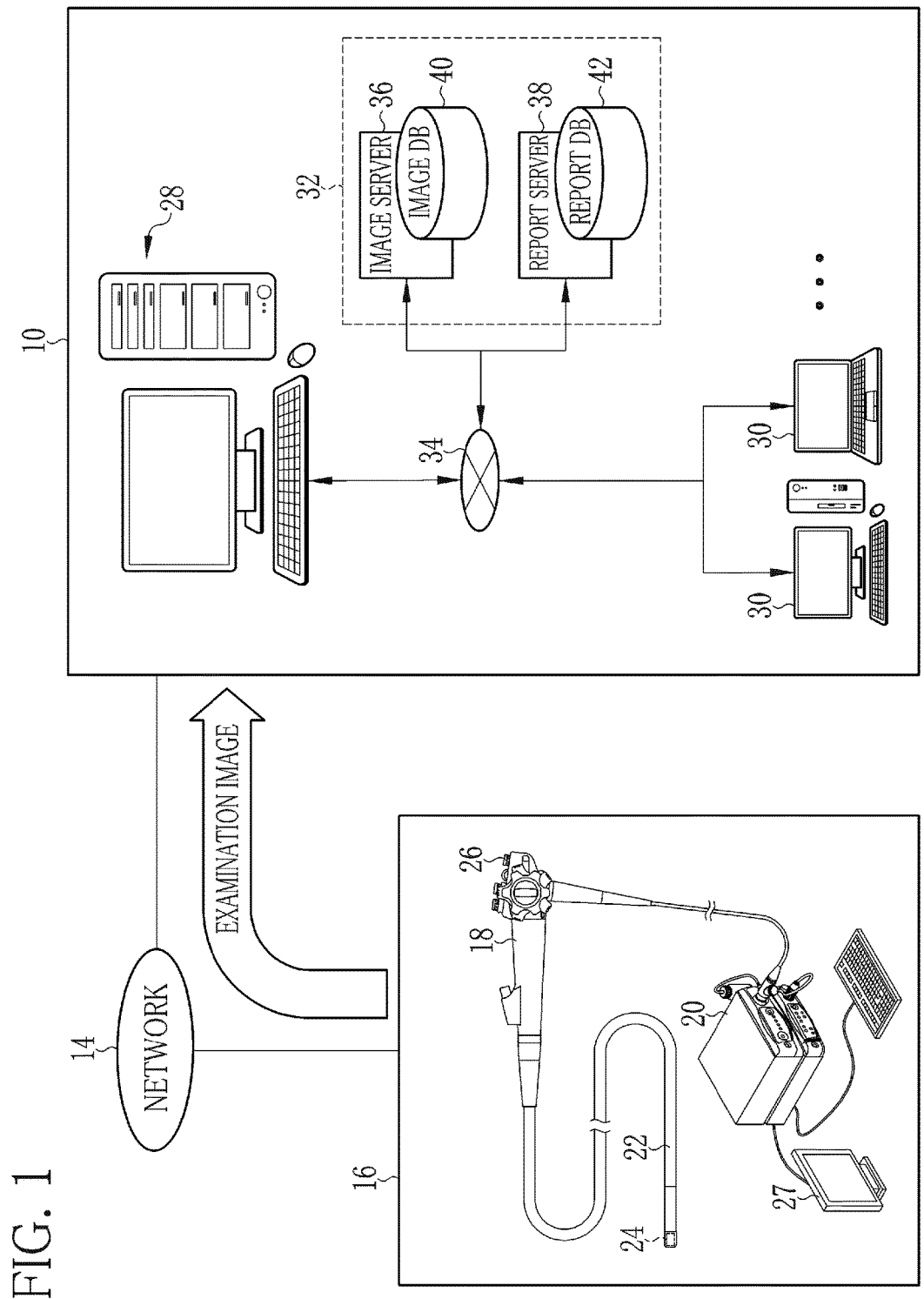
FIG. 1 is an explanatory view illustrating an image view support system.

An image view support system 10 (see FIG. 1) is a computer system that supports viewing examination images 12 (see FIG. 2) obtained in at least one endoscopic examination (hereinafter simply referred to as the examination). The image view support system 10 is connected to an endoscope system 16 through a network 14. The network 14 is, for example, a LAN (local area network) in a hospital.

The endoscope system 16 is used for performing the examination. The examination is performed by, for example, an endoscopist upon a request of a patient's doctor (clinician). The two or more examination images 12 are obtained or captured in the examination, which will be described below. The endoscopist selects at least one of the examination images 12 and prepares an examination report 44 (see FIG. 4), to which the at least one selected examination image 12 is attached. The examination report 44 and the examination images 12, which are obtained in the examination, are viewed by the clinician and the like and used for diagnosing the patient. Of the examination images 12 obtained in the examination, the examination image 12 attached to the examination report 44 may be referred to as the attached image 12A and the examination image 12 not attached to the examination report 44 may be referred to as the unattached image 12B to distinguish between the attached images 12A and the unattached images 12B.

The endoscope system 16 comprises an endoscope 18 and a processor device 20. An imaging unit 24 such as a CCD (charge coupled device) is incorporated in a distal end portion of an insertion section 22, which is to be inserted into a patient's body cavity, of the endoscope 18. The imaging unit 24 captures an image of the patient's body cavity. The imaging unit 24 is able to perform movie capture and still image capture. The movie capture is started when or immediately after the endoscope system 16 is turned on. The imaging unit 24 inputs the captured images (that is, frames), which constitute a movie, to the processor device 20. The processor device 20 generates a display image based on the inputted image and displays the display image on a display 27 in real time. The captured images (the movie) are displayed and stored.

The still image capture is performed in response to operation of an imaging button 26. In other words, still images may be captured at any timing. In addition, the endoscope system 16 is provided with a mode for automatically capturing the still images at predetermined time intervals (for example, at time intervals of three seconds). Before the examination, test image capture of the still images (test images) is performed as one of operation tests for the parts of the endoscope system 16.

In the case of the still image capture, the processor device 20 displays the still image on the display 27 and stores it. In the endoscope system 16, the movie and the still images are stored as the examination images 12. The examination images 12 include unnecessary images, which are unnecessary for diagnosis. The unnecessary images include those captured before the insertion section 22 is inserted into the body cavity, for example, the test images captured in the test image capture and the images captured immediately after the endoscope system 16 is turned on.

The endoscope system 16 is connected to the image view support system 10 through the network 14 such as the LAN in the hospital. The examination images 12 captured by the endoscope system 16 are stored in the image view support system 10.

The image view support system 10 comprises an image view support server apparatus 28, a client terminal apparatus 30, and a server cluster 32, which are connected through a network 34 such as a LAN. Based on a request from the client terminal apparatus 30, the image view support server apparatus 28 generates or updates a display screen 52, on which the at least one examination image 12 is displayed, and delivers the display screen 52 to the client terminal apparatus 30. The image view support server apparatus 28 is an example of an image view support apparatus.

The server cluster 32 comprises an image server 36 and a report server 38. The image server 36 comprises an image database (DB) 40. The image DB 40 is an example of an image storage unit. The image DB 40 (see FIG. 2) stores the examination images 12, which are transmitted from the endoscope system 16. The report server 38 comprises a report database (DB) 42. The report DB 42 is an example of a report storage unit. The report DB 42 (see FIG. 3) stores the examination reports 44. The examination report is prepared for each examination. In other words, the examination report 44 is prepared on a per endoscopic examination basis. Each of the image DB 40 and the report DB 42 enables a search based on a keyword such as a patient ID (identification data) assigned to each patient or an examination ID assigned to each examination.

The examination report 44 is a report in which findings from the at least one examination image 12 are described. The examination report 44 is written by a doctor, for example, the endoscopist who performed the examination and viewed the examination images 12. The at least one endoscopic image 12 based on which the examination report 44 is written is attached to the examination report 44.

The client terminal apparatus 30 is used for viewing the examination images 12 and the examination report 44. The endoscopist uses the client terminal apparatus 30 to view the examination images 12 and to prepare the examination report 44 after the examination. The doctor (clinician) of a clinical department who requested the examination uses the client terminal apparatus 30 to view the examination images 12 and the examination report 44. The client terminal apparatus 30 is, for example, a notebook computer or a desktop computer. In a case of referring to results of past examinations (e.g. in a case of a medical follow-up or the like), the doctor uses the client terminal apparatus 30 to access the image view support server apparatus 28. The doctor views the stored examination images 12 and the stored examination report 44 read from the image view support server apparatus 28.

Figure 2:
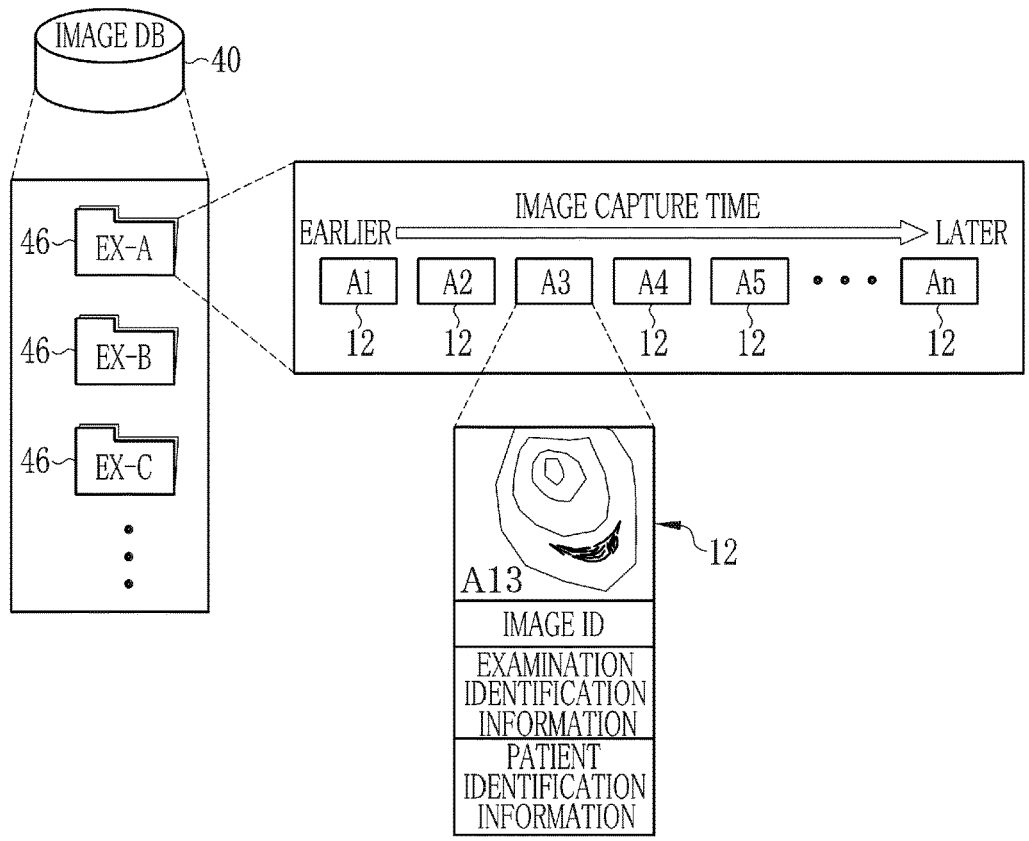
FIG. 2 is an explanatory view illustrating content of an image database (DB)

As illustrated in FIG. 2, the image DB 40 comprises two or more image folders 46. One image folder 46 is created every time an endoscopic examination is performed. In FIG. 2, "EX-A", "EX-B", and "EX-C" are abbreviations for "examination A", "examination B", and "examination C", respectively. The image folders 46 correspond to the respective endoscopic examinations. Each image folder 46 stores the examination images 12 that are obtained in the corresponding endoscopic examination. As described above, in the endoscopic examination, various types of image capture, for example, the movie capture, the still image capture in response to the operation of the imaging button 26, the automatic still image capture at predetermined time intervals, and the test image capture may be performed. All of the images obtained in one examination, in other words, all of the images, which may include those obtained by the various types of image capture, are stored as the examination images 12 in the image folder 46.

An image ID and image capture time (the time at which the examination image 12 is captured or recorded) are recorded as supplementary information on each of the examination images 12. The image capture time, which is recorded as the supplementary information on each examination image 12, is used for determining an order of the examination images 12 to be displayed.

FIG. 2 illustrates an example in which the image folder 46 corresponding to the examination A stores "n" examination images 12 with the image IDs "A1" to "An". Here, suffixes (1 to n) added to "A" of the image IDs "A1" to "An" are assigned in an ascending order of the image capture time. In FIG. 2, the image ID of the examination image 12 captured at the earliest image capture time is A1. The image IDs of the examination images 12 captured at the subsequent image capture times are A2, A3, and so forth.

The supplementary information is attached to each examination image 12 in the image folder 46. The supplementary information includes the image ID, examination identification information (e.g. the examination ID, type of the examination, or the like) for identifying the examination in which the examination images 12 are obtained, and patient identification information (e.g. the patient ID, patient name, or the like) for identifying the patient imaged in the examination images 12. For example, the examination identification information and the patient identification information are included in an examination order, which is inputted to the processor device 20 before the start of the examination. The examination identification information and the patient identification information are read from the examination order and attached to the examination image 12.

Before or at the time the examination images 12 transmitted from the endoscope system 16 are stored in the image server 36, the image folder 46 is created in the image server 36. The examination images 12 are stored on a per endoscopic examination basis. In other words, the examination images 12 are stored on an examination by examination basis. Alternatively, the endoscope system 16 may create the image folder 46. The image server 36 may receive each image folder 46 created. In a case where the image DB 40 stores the examination images 12 such that the examination images 12 are read (retrieved) on the examination by examination basis, the image folder 46 may be unnecessary.

Figure 3:
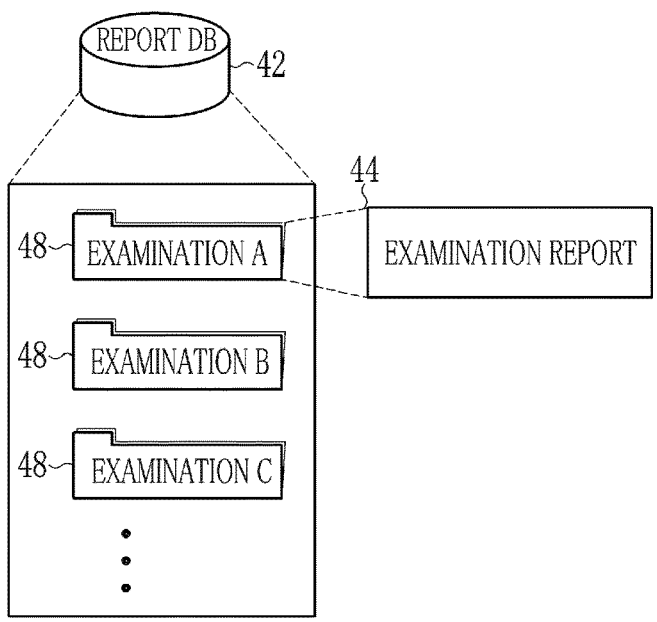
FIG. 3 is an explanatory view illustrating content of a report database (DB)

As illustrated in FIG. 3, the report DB 42 comprises two or more report folders 48. The report folder 48 stores the examination report 44, which is prepared on a per endoscopic examination basis (that is, on an examination by examination basis). In a case where the report DB 42 stores the examination reports 44 such that the examination report 44 is read (retrieved) on the examination by examination basis, the report folder 48 may be unnecessary.

Figure 4:
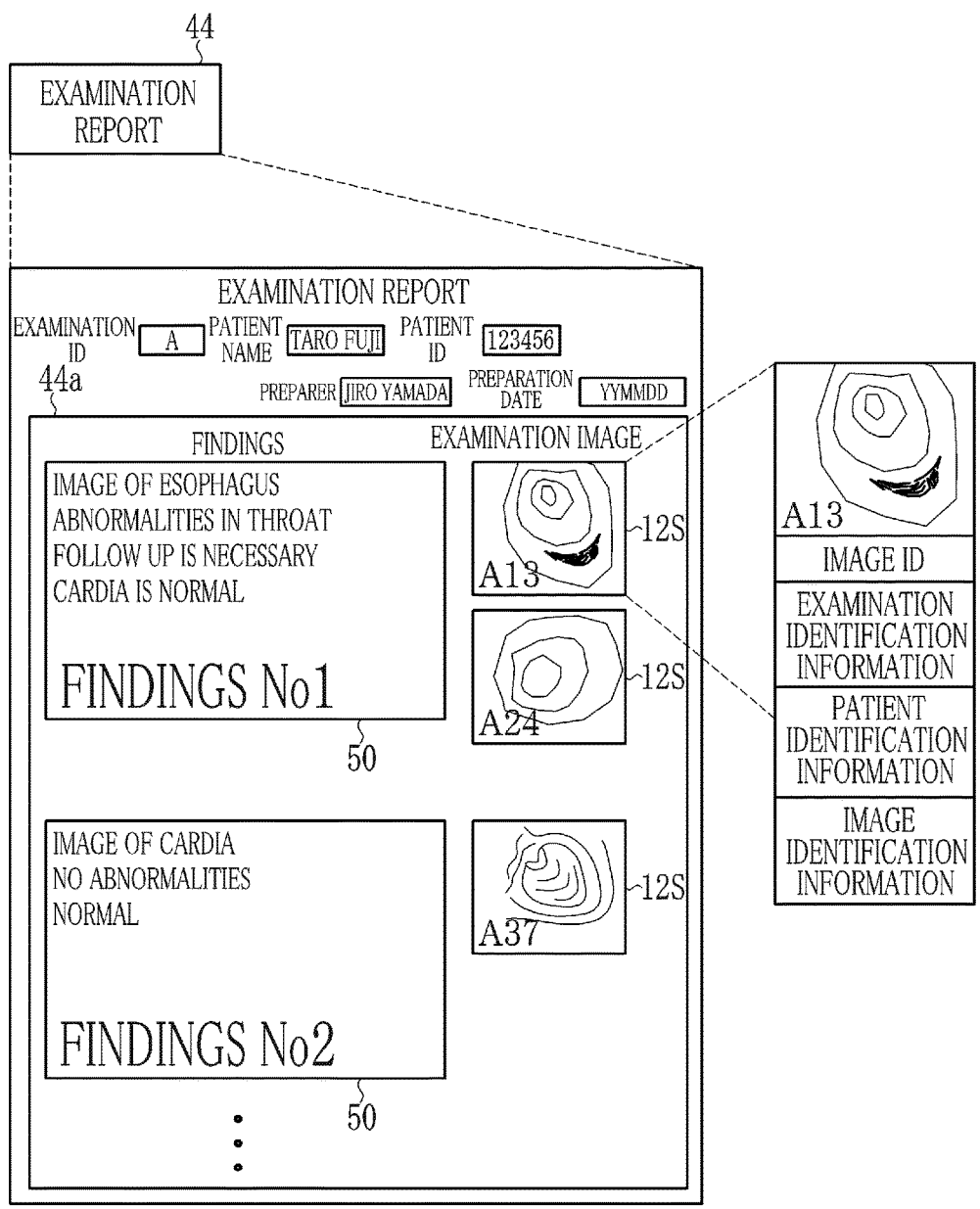
FIG. 4 is an explanatory view illustrating content of an examination report.

As illustrated in FIG. 4, the examination report 44 comprises a report's main body 44*a*, the examination identification information, the patient identification information, and report preparer information. The report preparer information represents a person (preparer) who prepared the examination report 44. The main body 44*a* comprises findings 50 of the endoscopist and the at least one examination image 12 attached to the examination report 44. The examination image 12 attached to the examination report 44 is the basis for the findings 50. The attached examination image 12 is associated with the corresponding findings 50. In FIG. 4, the examination images 12 with the image IDs "A13" and "A24" are associated with the findings 50 (findings No. 1 in the drawing). The examination image 12 with the image ID "A37" is associated with the second findings 50 (findings No. 2 in the drawing).

In preparing the examination report 44, the endoscopist inputs the findings 50 while observing the examination images 12 obtained in the examination. To the examination report 44, the endoscopist attaches the at least one examination image 12 that is the basis for the findings 50. For example, a thumbnail form of the examination image 12 is attached to the examination report 44. In other words, the examination image 12 is converted into a thumbnail image 12S and the thumbnail image 12S is attached to the examination report 44.

The image ID of the examination image 12 that is the original image of the thumbnail image 12S is attached as the image identification information to the thumbnail image 12S. In the case where the examination report 44 is read, the image identification information enables identifying the examination image 12 attached to the examination report 44, from among the plurality of the examination images 12 captured or obtained in the examination corresponding to the examination report 44. FIG. 4 illustrates an example in which the three examination images 12 with the image IDs "A13", "A24", and "A37" are attached to the examination report 44 of the examination A. Note that, in the drawings, the characters (e.g. "A13", "A24", and "A37") are attached to the examination images 12 for the sake of convenience in the description. The characters are not displayed in the actual examination images 12 displayed.

In this example, the examination image 12 is converted into the thumbnail form and attached to the examination report 44. Alternatively, the examination image 12, which is stored in the image folder 46, or a copy thereof may be attached, without the conversion into the thumbnail form, to the examination report 44. An address (e.g. an address of the storage storing the examination image 12) for accessing the examination image 12 may be recorded, instead of the examination image 12 itself, on the examination report 44. "Attaching the examination image 12 to the examination report 44" includes recording the information for accessing the examination image 12 on the examination report 44. In this case, the information for accessing the examination image 12 functions as the image identifying information.

Each of the image view support server apparatus 28, the client terminal apparatus 30, the image server 36, and the report server 38 is comprised of a computer (e.g. a personal computer, a server computer, a workstation, or the like) installed with a control program (e.g. an operating system) and an application program (e.g. a client program or a server program).

Figure 5:
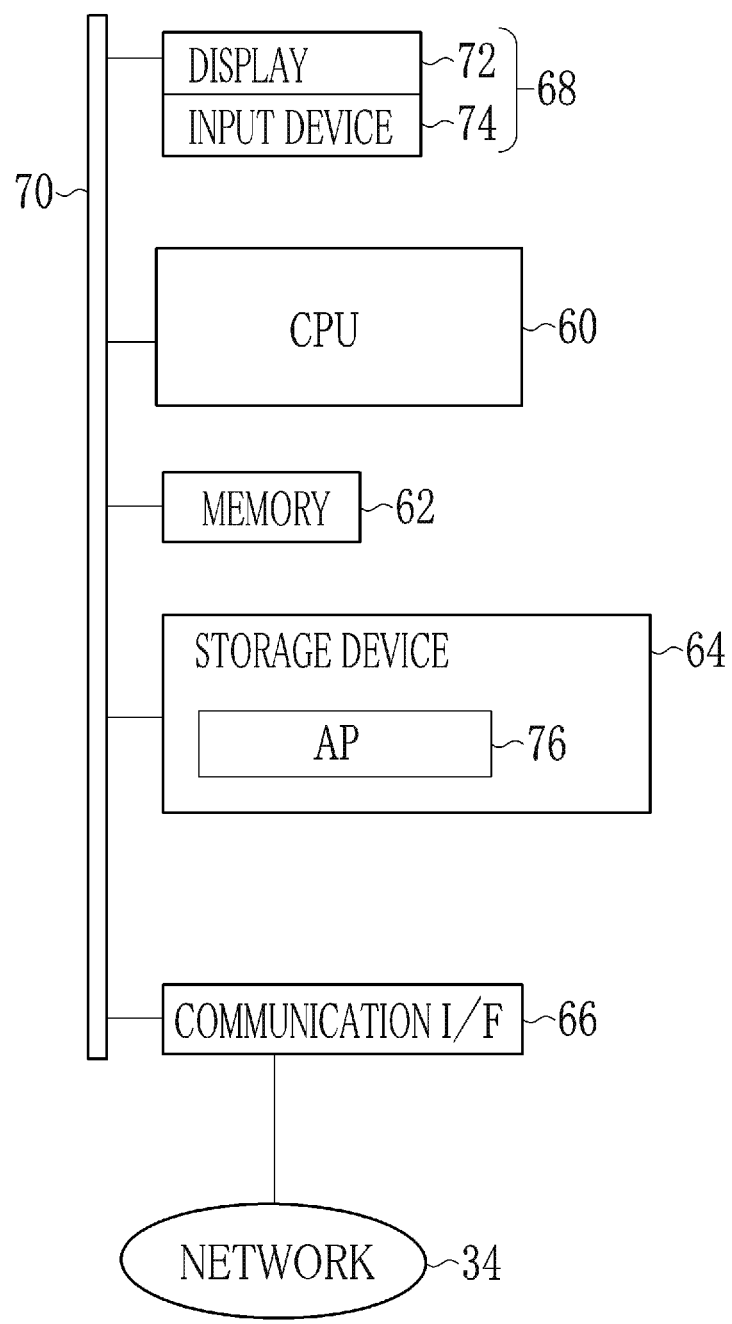

As illustrated in FIG. 5, the computers, which constitute the image view support server apparatus 28, the image server 36, the report server 38, and the client terminal apparatus 30, respectively, have substantially the same configuration. Each computer comprises a CPU (Central Processing Unit) 60, a memory 62, a storage device 64, a communication I/F 66, and an input and output unit 68, which are connected through a data bus 70. The input and output unit 68 comprises a display 72 and an input device 74 such as a keyboard and a mouse.

The storage device 64 is, for example, an HDD (hard disk drive) and stores the control program and an application program (AP) 76. The DBs 40 and 42 are constructed in the image server 36 and the report server 38, respectively. Each of the image server 36 and the report server 38 is provided with the storage device 64 for the DB 40 or 42, in addition to the HDD for storing the programs. The storage device 64 is, for example, a disk array with two or more HDDs connected. Note that the disk array may be incorporated in a server body. The disk array may be provided separately from the server body and connected to the server body through a network such as the LAN.

The memory 62 is a working memory, which is used by the CPU 60 to execute processing. The memory 62 is composed of RAM (random access memory). The CPU 60 loads the control program, which is stored in the storage device 64, into the memory 62 and executes the processing in accordance with the program. Thereby the CPU centrally controls each section of the computer. The communication I/F 66 is a network interface, which controls the transmission to and from the network 14.

The client program is installed as the AP 76 on the client terminal apparatus 30. The client program is a program that allows the client terminal apparatus 30 to execute various functions. The various functions include a function to access the image view support server apparatus 28 and transmit various requests such as a delivery request and an update request for the display screen 52, and a function to receive the display screen 52, which is delivered from the image view support server apparatus 28 to the client terminal apparatus 30, and display the display screen 52. Note that the client program may be a program used exclusively for the image view support system 10 or a well-known web browser.

Figure 6:
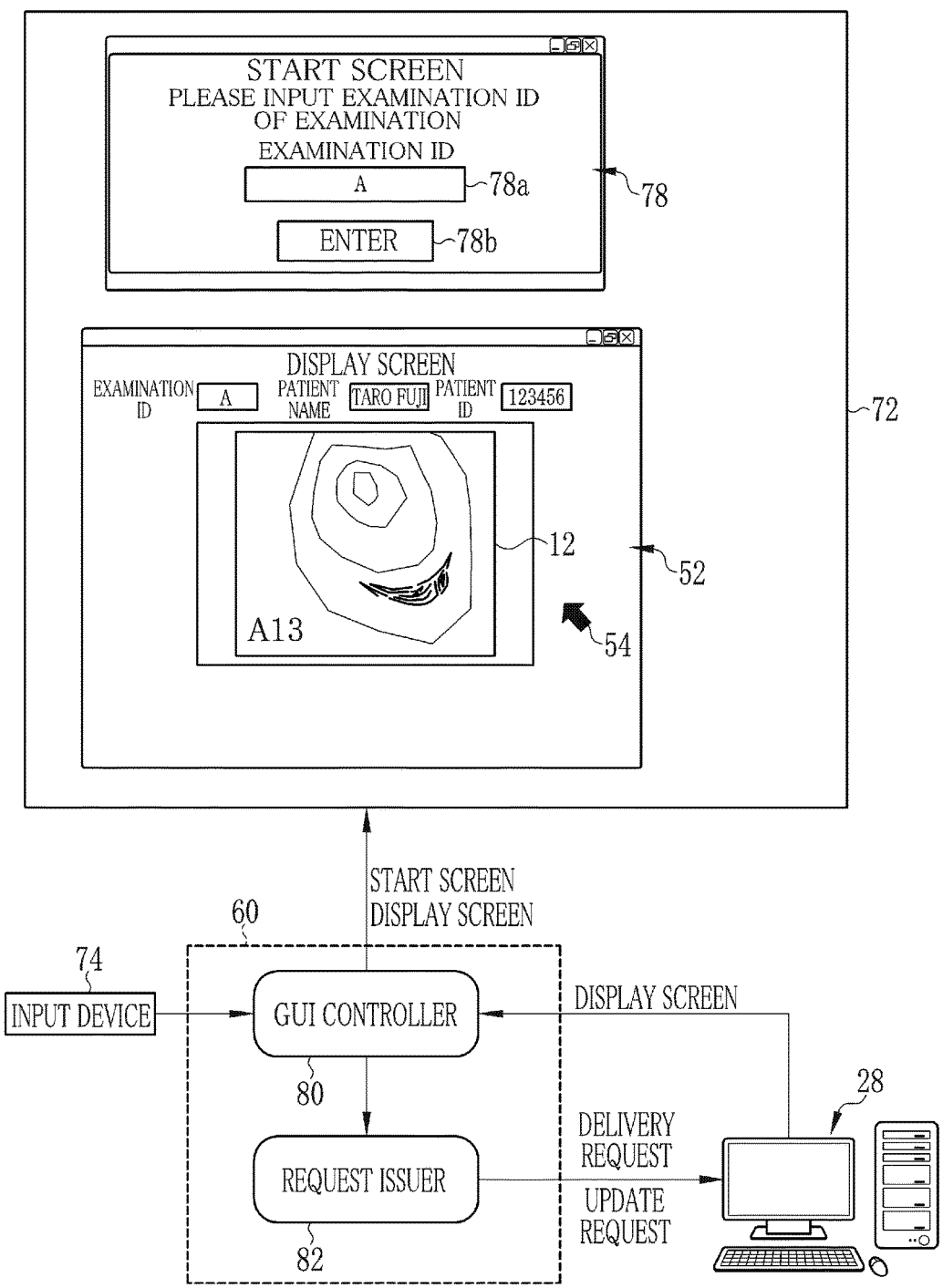
FIG. 6 is an explanatory view illustrating functions of a client terminal apparatus.

As illustrated in FIG. 6, in response to the start of the client program, the display 72 of the client terminal apparatus 30 displays a start screen 78. The start screen 78 comprises an operation function provided by a GUI (graphical user interface). The CPU 60 of the client terminal apparatus 30 works together with the memory 62 and the like, and thereby the CPU 60 functions as a GUI controller 80 and a request issuer 82. The request issuer issues the various requests to the image view support server apparatus 28.

The start screen 78 comprises an examination ID input box 78*a* and an enter button 78*b*. The examination ID is inputted to the examination ID input box 78*a* and the enter button 78*b* is operated. Thereby one examination corresponding to the input examination ID is designated (selected) from among the plurality of the examinations. In response to designating the examination, the information inputted to the examination ID input box 78*a* is transmitted from the GUI controller 80 to the request issuer 82. The request issuer 82 generates the delivery request for delivery of the display screen 52 that displays the examination images 12 obtained in the examination corresponding to the examination ID inputted to the examination ID input box 78*a*. The request issuer 82 issues the delivery request to the image view support server apparatus 28. In response to the delivery request, the image view support server apparatus 28 delivers the display screen 52 of an initial state to the client terminal apparatus 30 that sent the delivery request. The display screen 52 is displayed on the display 72 of the client terminal apparatus 30.

The display screen 52 is composed of data described by a markup language such as XML (Extensible Markup Language), for example. The display screen 52 itself has the operation function provided by the GUI. The GUI controller 80 receives operation instructions (e.g. a click operation of the operation button by a pointer 54 of the mouse) from the input device 74 through the display screen 52. The request issuer 82 issues the update request (or the like) for the display screen 52 in response to the operation instruction received by the GUI controller 80.

The update request includes an instruction to update content displayed on the display screen 52. For example, the update request includes an instruction to switch the examination image 12 displayed, an instruction to switch a display mode, or the like. In response to the transmission of the update request to the image view support server apparatus 28, the image view support server apparatus 28 updates the display screen 52 and delivers the updated display screen 52 to the client terminal apparatus 30. Thereby the display screen 52 displayed on the client terminal apparatus 30 is updated.

The display screen 52 displays, for example, the examination image 12, the examination ID of the examination, and the name and the patient ID of the patient who is the subject of the examination.

Figure 7:
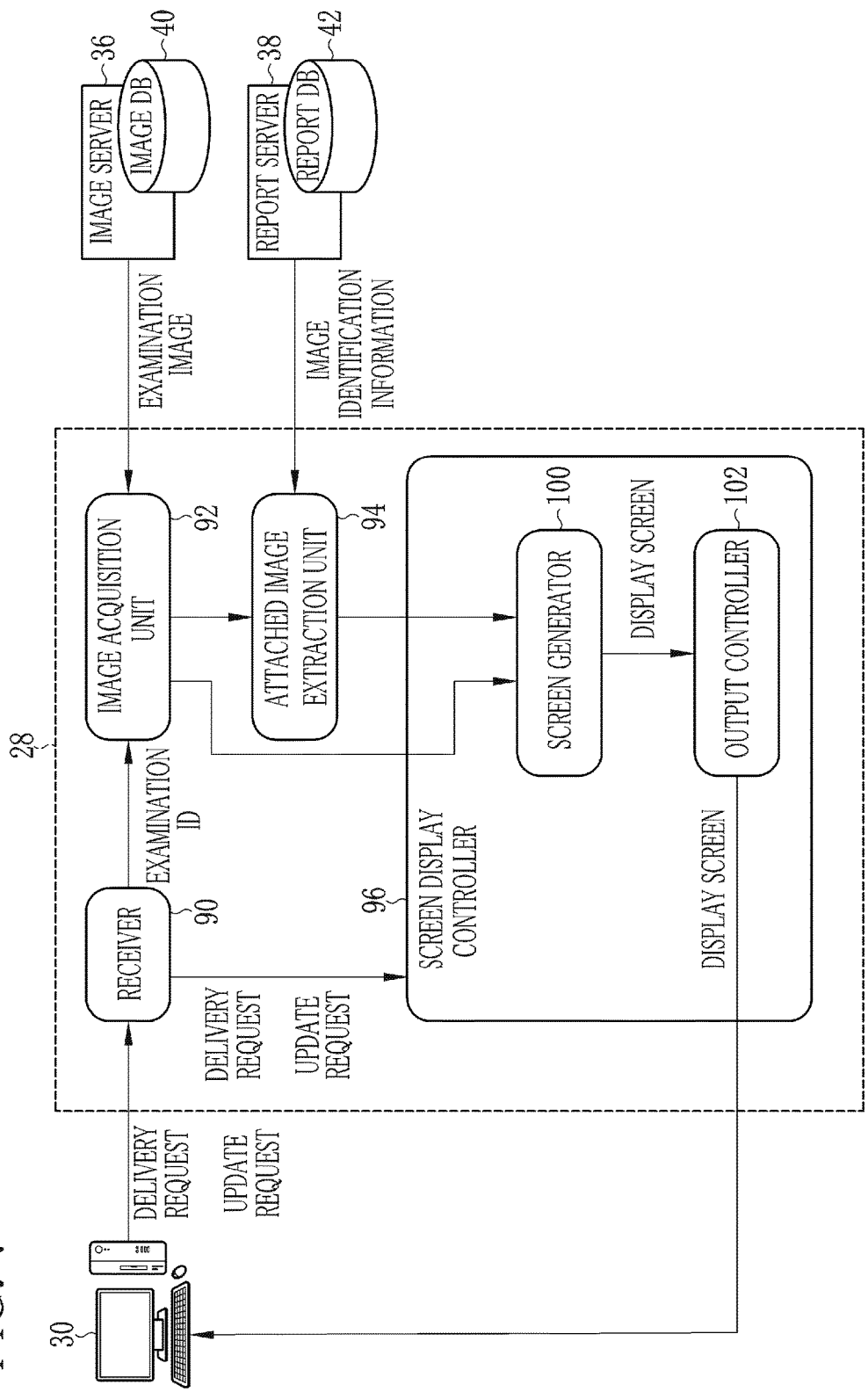
FIG. 7 is an explanatory view illustrating functions of the image view support server apparatus.

As illustrated in FIG. 7, the server program is installed as the AP 76 on the image view support server apparatus 28. The server program is an operation program that allows the computer to function as the image view support server apparatus 28 (the image view support apparatus). In response to the start of the server program, the CPU 60 of the image view support server apparatus 28 works together with the memory 62 and the like, and thereby the CPU 60 functions as a receiver 90, an image acquisition unit 92, an attached image extraction unit 94, and a screen display controller 96.

The receiver 90 receives the delivery request and the update request for the display screen 52. The delivery request and the update request are inputted from the client terminal apparatus 30. The receiver 90 outputs the delivery request and the update request to the screen display controller 96. As described above, the delivery request for the display screen 52 requests the delivery of the display screen 52, which displays the examination images 12 obtained in the examination designated by the examination ID that is inputted to the examination ID input box 78*a* in the start screen 78. In other words, the receiver 90 functions as an examination designation receiver, which receives a designation operation for designating one endoscopic examination from among the endoscopic examinations. In response to receiving the delivery request, the receiver 90 inputs the examination ID (that is, the examination ID inputted to the examination ID input box 78*a*) designated or specified by the delivery request, to each of the image acquisition unit 92 and the attached image extraction unit 94.

In response to the input of the examination ID, the image acquisition unit 92 accesses the image server 36 and acquires all of the examination images 12 that are obtained in the examination corresponding to the examination ID inputted. To be more specific, the image acquisition unit 92 uses the inputted examination ID as a search keyword to perform a search in the image DB 40 and reads the examination images 12 having the inputted examination ID from the image DB 40. Thereby the image acquisition unit 92 acquires all of the examination images 12 obtained in the one examination. The image acquisition unit 92 outputs the acquired examination images 12 to the screen display controller 96 and the attached image extraction unit 94.

In response to the input of the examination ID, the attached image extraction unit 94 accesses the report server 38 and reads the examination report 44 of the examination corresponding to the inputted examination ID. Based on the examination report 44, the attached image extraction unit 94 extracts the at least one examination image 12 (that is, the at least one attached image 12A) attached to the examination report 44, from the plurality of examination images 12 acquired from the image DB 40.

The screen display controller 96 comprises a screen generator 100 and an output controller 102. The examination image 12 is directly inputted from the image acquisition unit 92 to the screen generator 100. The attached image 12A is inputted from the attached image extraction unit 94 to the screen generator 100. The screen generator 100 generates and updates the display screen 52, which displays the inputted attached image(s) 12A or the examination images 12 including the attached image(s) 12A.

The generated or updated display screen 52 is outputted to the output controller 102. The output controller 102 delivers the inputted display screen 52 to the client terminal apparatus 30 that sent the delivery request or the update request. The client terminal apparatus 30 displays the display screen 52, which is delivered from the output controller 102, on the display 72.

The display screen 52 has two display modes: a report image display mode and an entire image display mode. The report image display mode is an example of a first display mode. The entire image display mode is an example of a second display mode. In the report image display mode, only the attached images 12A are extracted from the examination images 12 obtained in the one examination, and the extracted attached images 12A are displayed in the chronological order. In the entire image display mode, all of the examination images 12 that are obtained in the one examination are displayed. In other words, in the entire image display mode, the attached images 12A and the unattached images 12B, which are the examination images 12 not attached to the examination report 44, are displayed in the chronological order.

Figure 8:
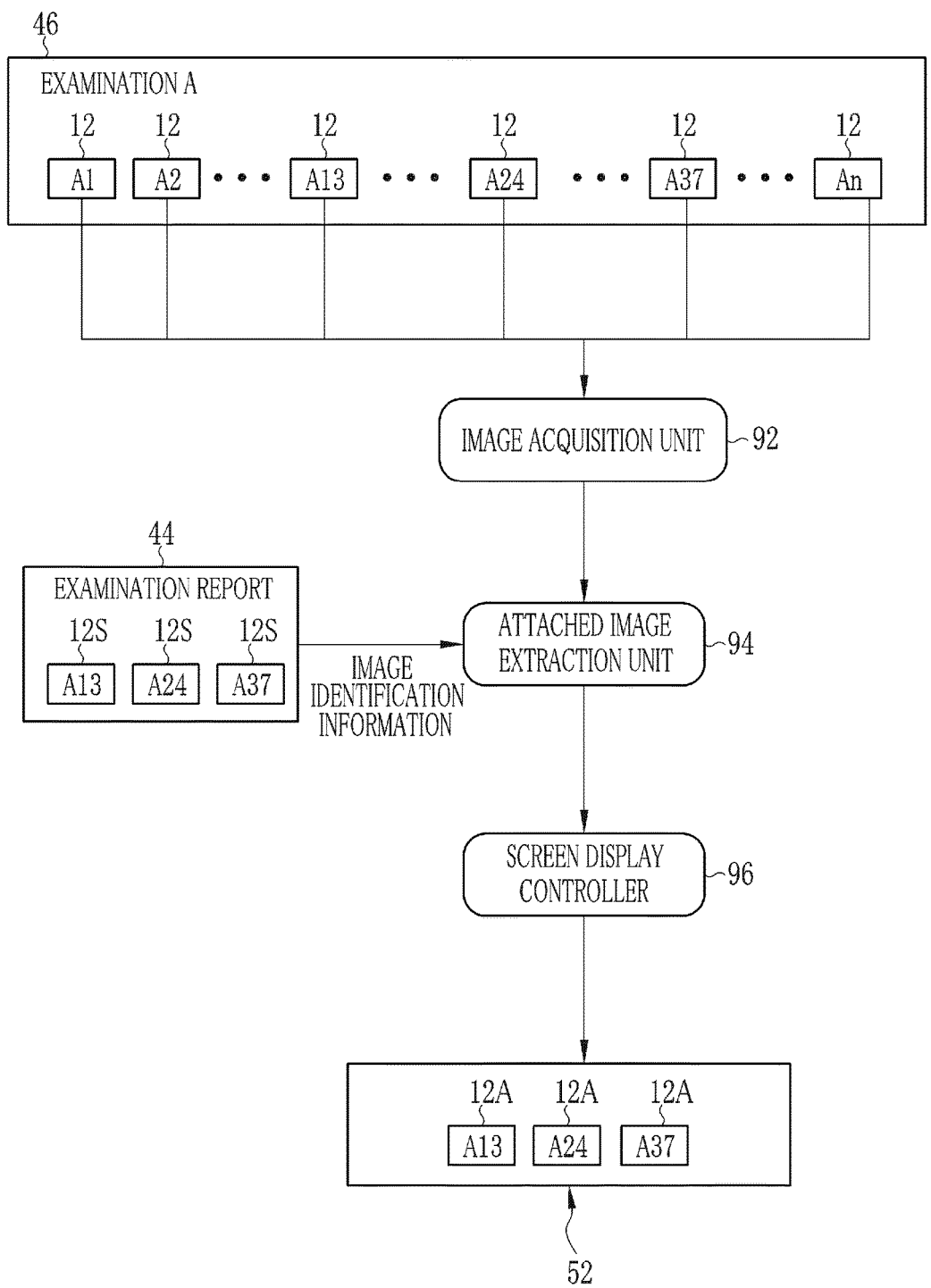
FIG. 8 is an explanatory view illustrating a procedure in a report image display mode.

As illustrated more specifically in FIG. 8, the attached image extraction unit 94 reads the image identification information from the supplementary information of the thumbnail images 12S attached to the examination report 44. Based on the image identification information, the attached image extraction unit 94 extracts the attached images 12A. The attached image extraction unit 94 outputs the attached images 12A to the screen display controller 96. The screen display controller 96 generates the display screen 52 that displays only the inputted attached images 12A. The screen display controller 96 refers to the image capture time of each of the attached images 12A to display the attached images 12A in the chronological order of the image capture time.

For example, in a case where the three thumbnail images 12S with the image IDs "A13", "A24", and "A37" are attached to the examination report 44, the display screen 52 displays only the three attached images 12A with the image IDs "A13", "A24", and "A37" in the chronological order.

Figure 9:
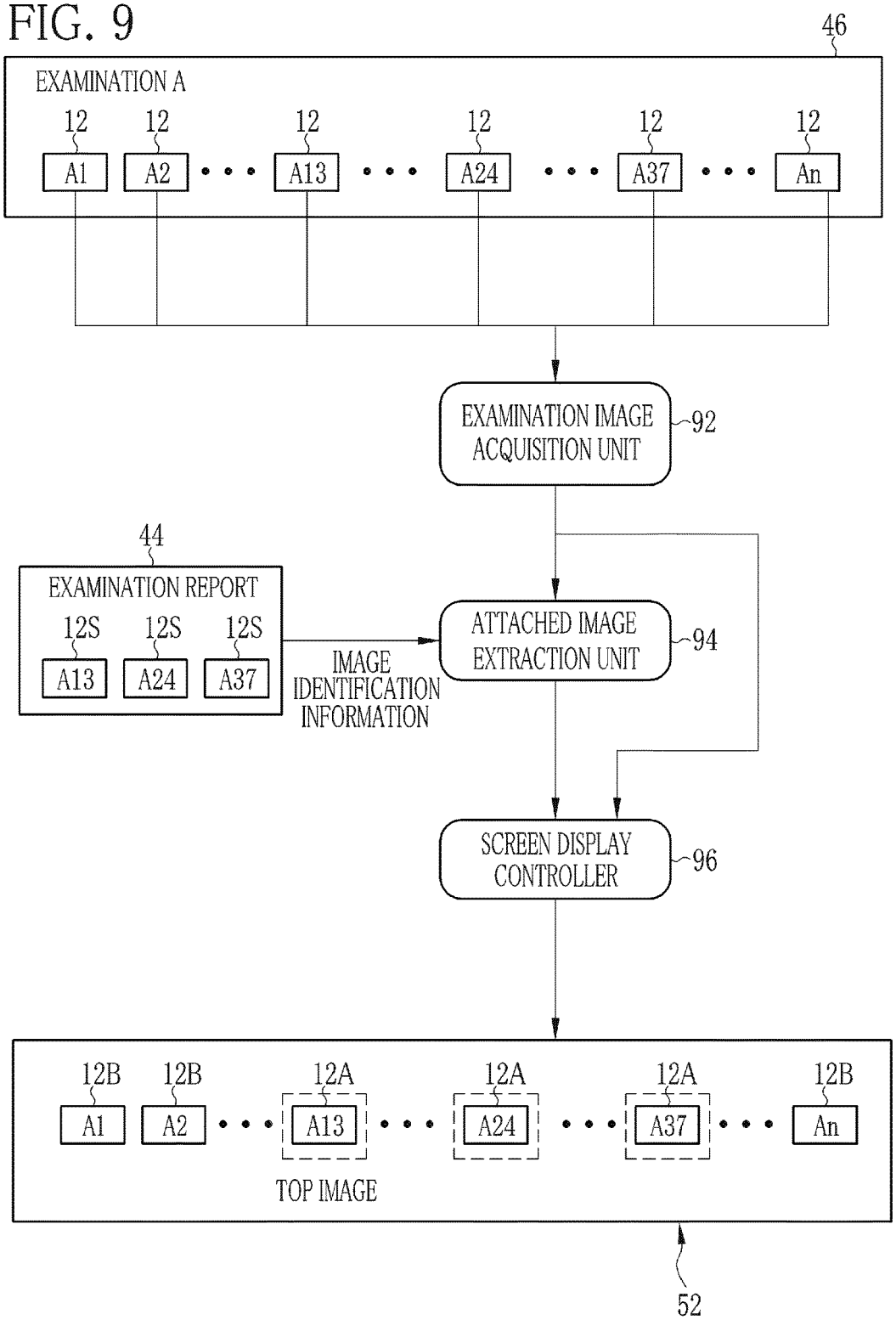
FIG. 9 is an explanatory view illustrating a procedure in an entire image display mode.

In the entire image display mode illustrated in FIG. 9, all of the examination images 12 corresponding to the one examination, which are acquired by the image acquisition unit 92, are inputted to the screen display controller 96. The screen display controller 96 displays all of the acquired examination images 12 in the chronological order of the image capture time on the display screen 52.

In the entire image display mode, the attached image extraction unit 94 inputs the image identification information, which is read from the examination report 44, to the screen display controller 96. Based on the image identification information, the screen display controller 96 identifies the attached images 12A and the unattached images 12B from among the inputted examination images 12. The screen display controller 96 selects the attached image 12A with the earliest image capture time as a top image, which is to be displayed at the top in the chronological order.

Figure 10:
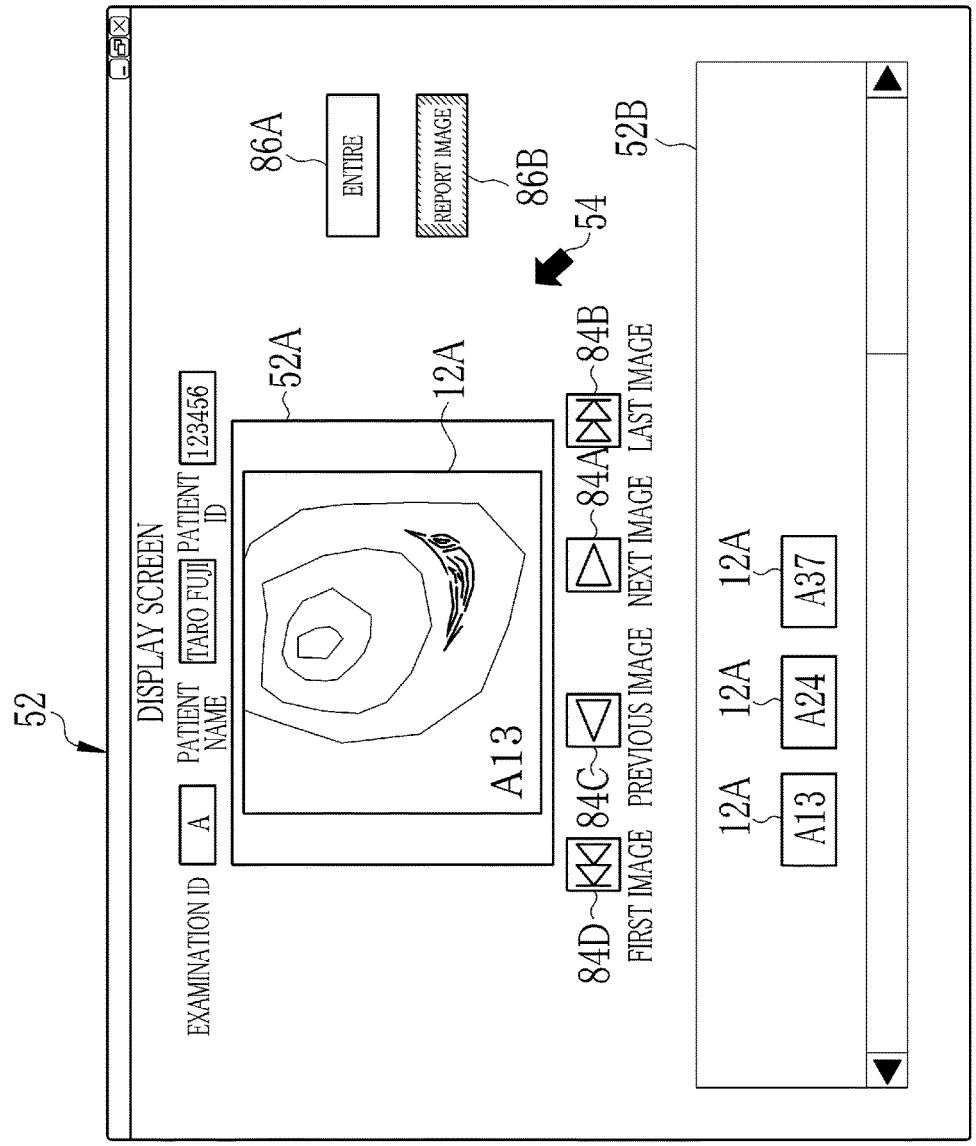
FIG. 10 is an explanatory view illustrating a display screen in the report image display mode.
Figure 11:
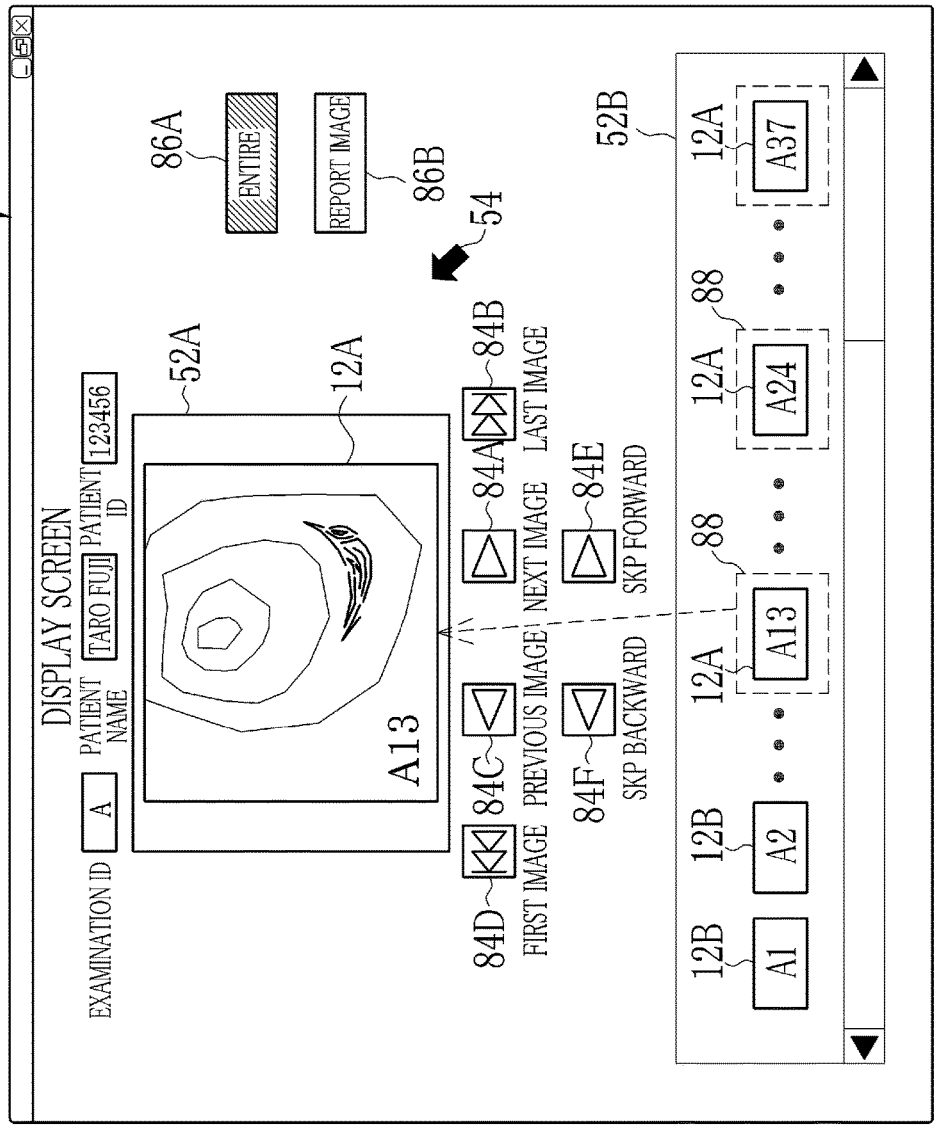
FIG. 11 is an explanatory view illustrating a display screen in the entire image display mode.

FIGS. 10 and 11 illustrate specific examples of the display screens 52 in the report image display mode and the entire image display mode. As illustrated in FIGS. 10 and 11, the display screen 52 displays the examination identification information (e.g. the examination ID "A" of the examination A) and the patient identification information. The display screen 52 comprises a switch display area 52A and an arrangement display area 52B.

In the switch display area 52A, the examination images 12 are selectively displayed one at a time in the chronological order of the image capture time. In the arrangement display area 52B, the examination images 12 arranged in the chronological order of the image capture time are displayed.

In the report image display mode illustrated in FIG. 10, only the extracted attached images 12A are displayed in the chronological order in the arrangement display area 52B. In the switch display area 52A, the attached images 12A in the arrangement display area 52B are selectively displayed one at a time.

In the entire image display mode illustrated in FIG. 11, all of the examination images 12 (including the attached images 12A and the unattached images 12B) obtained in the one examination are displayed in the chronological order in the arrangement display area 52B. In the switch display area 52A, the two or more examination images 12 in the arrangement display area 52B are selectively displayed one at a time.

Operation buttons 84A to 84D are provided below the switch display area 52A. The operation buttons 84A to 84D are operated to switch the examination image 12 displayed in the switch display area 52A. In the chronological order, a "previous image" represents the examination image 12 captured at an earlier image capture time and a "next image" represents the examination image 12 captured at a later image capture time. The operation button 84A is operated to perform a single-frame (frame-by-frame) advance within the examination images 12 displayed in the switch display area 52A. In other words, the examination image 12 displayed in the switch display area 52A is advanced by one frame and the "next image" is displayed by operating the operation button 84A. The operation button 84B is operated to switch the examination image 12 displayed in the switch display area 52A to the last examination image 12, which is placed at the end in the chronological order displayed in the arrangement display area 52B.

The operation button 84C is operated to perform a single-frame (frame-by-frame) rewind within the examination images 12 displayed in the switch display area 52A. In other words, the examination image 12 displayed in the switch display area 52A returns to the "previous image". Namely, the operation button 84C has a function reverse to that of the operation button 84A. The operation button 84D is operated to switch the examination displayed in the switch display area 52A to the first examination image 12 (the top image), which is placed at the top in the chronological order displayed in the arrangement display area 52B. The operation button 84D has a function reverse to that of the operation button 84B.

In the report image display mode illustrated in FIG. 10, one of the operation buttons 84A to 84D is operated to perform the single-frame advance, the single-frame rewind, or the like within the attached images 12A. In the entire image display mode illustrated in FIG. 11, the single-frame advance, the single-frame rewind, or the like is performed within the examination images 12 corresponding to the one examination.

In the entire image display mode illustrated in FIG. 11, operation buttons 84E and 84F are provided in addition to the operation buttons 84A to 84D. The operation buttons 84E and 84F are operated to skip the unattached images 12B and perform the single-frame advance or rewind within only the attached images 12A. In the entire image display mode, the attached images 12A and the unattached images 12B are mixed in the arrangement display area 52B. Operating the operation button 84E or 84F enables the single-frame advance or rewind within only the attached images 12A in the switch display area 52A.

The display screen 52 is provided with mode selection buttons 86A and 86B. For example, the mode selection button 86B is operated to switch the mode to the report image display mode illustrated in FIG. 10. The mode selection button 86A is operated to switch the mode to the entire image display mode illustrated in FIG. 11. Thus the mode is switched.

In the entire image display mode illustrated in FIG. 11, a mark 88 is provided to each attached image 12A in the arrangement display area 52B so as to distinguish the attached images 12A from the unattached images 12B. In the entire image display mode, in which the attached images 12A and the unattached images 12B are mixed, the marks 88 function as indexes. Thus the attached images 12A are viewed easily.

Figure 12:
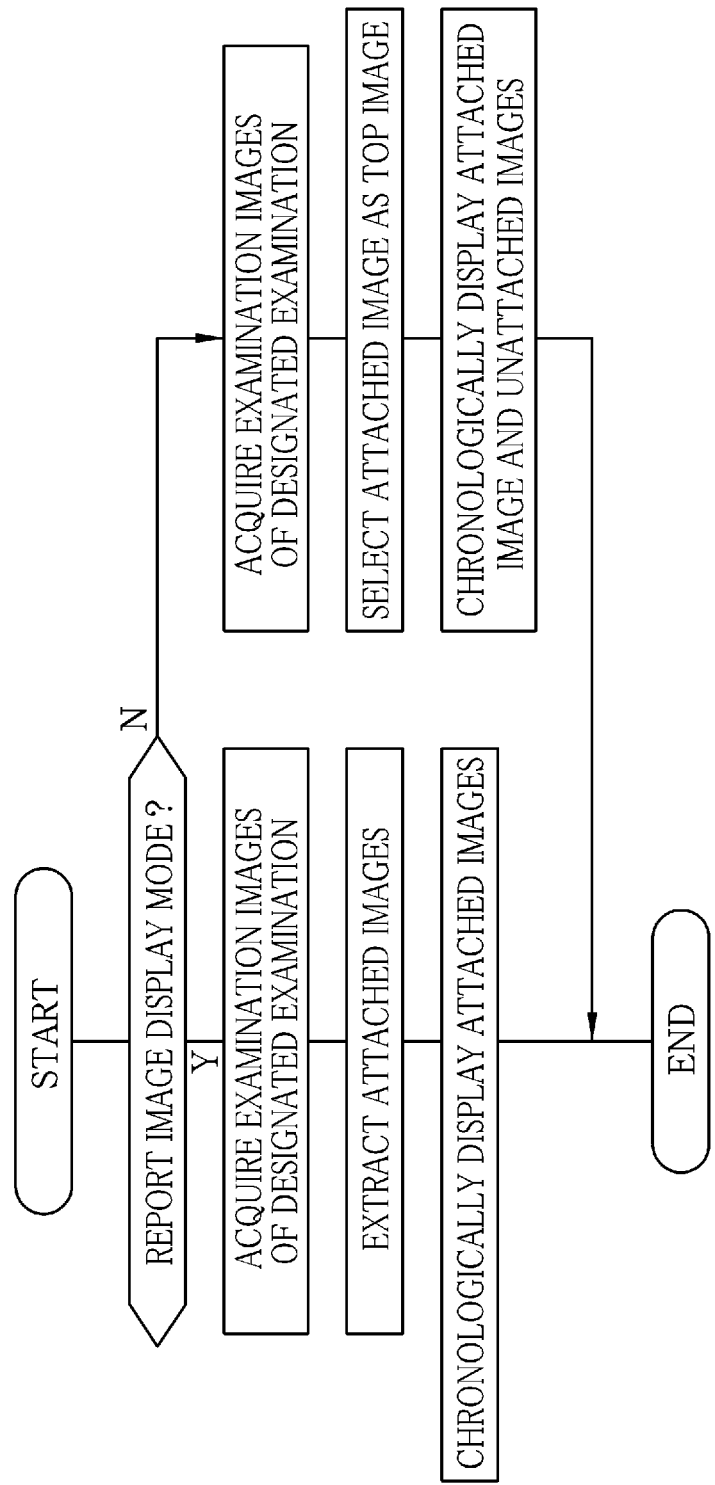
FIG. 12 is a flowchart illustrating an example of a procedure in an embodiment.

Hereinafter, referring to a flowchart in FIG. 12, an operation of the above-described configuration is described. In the case where the examination images 12 are to be viewed using the image view support system 10, the examination ID is inputted to the start screen 78 (see FIG. 6) of the client terminal apparatus 30. In response to this, the delivery request is issued. The image view support server apparatus 28 acquires all of the examination images 12 that are obtained in the examination with the inputted (designated) examination ID, from the image DB 40. The screen display controller 96 generates the display screen 52 of the entire image display mode shown in FIG. 11, for example.

During or at the time of the generation of the display screen 52, the screen display controller 96 selects the attached image 12A as the top image to be displayed at the top in the chronological order, based on the image identification information inputted from the attached image extraction unit 94. The screen display controller 96 displays the attached images 12A and the unattached images 12B in the chronological order on the display screen 52. The screen display controller 96 delivers the display screen 52 to the client terminal apparatus 30.

In the entire image display mode, the examination images 12 (including the attached images 12A and the unattached images 12B) obtained in the one examination are arranged in the chronological order in the arrangement display area 52B. In the arrangement display area 52B, each attached image 12A is displayed with the mark 88, so that the attached images 12A are easily distinguished from the unattached images 12B. Thereby the attached images 12A, which are the examination images 12 significant or relevant to the diagnosis, are viewed easily.

In the entire image display mode, the attached image 12A captured or recorded at the earliest image capture time among the attached images 12A is selected as the top image. The selected top image is displayed in the switch display area 52A. The attached image 12A is displayed as the top image in the switch display area 52A, so that the significant examination image 12 (that is, the attached image 12A) is viewed at a first glance. With the operation of the operation button 84E or 84F, the unattached images 12B are skipped and the single frame advance or rewind is performed only within the attached images 12A. Thus, the significant examination images 12 are viewed easily.

In response to the operation of the mode selection button 86B on the display screen 52, the update request is transmitted from the client terminal apparatus 30 to the image view support server apparatus 28. Upon receipt of the update request by the image view support server apparatus 28, the attached image extraction unit 94 reads the image identification information from the examination report 44 and extracts the attached images 12A from the examination images 12. The screen display controller 96 generates the display screen 52 on which only the extracted attached images 12A are displayed in the chronological order. The screen display controller 96 delivers the display screen 52 to the client terminal apparatus 30.

In the report image display mode illustrated in FIG. 10, only the attached images 12A are displayed in the chronological order in the arrangement display area 52B on the display screen 52. In the switch display area 52A, the attached images 12A are selectively and chronologically displayed one at a time. Thereby the examination images 12 that are significant or relevant to the diagnosis are viewed quickly.

The examination images 12, which are stored on a per endoscopic examination basis (on an examination by examination basis), may include the test images captured in the test image capture and the movie and still images captured before the insertion of the insertion section 22 into the body cavity. There are cases where the automatic still image capture, in which the still images are captured automatically at predetermined time intervals, may start before the insertion of the insertion section 22 into the body cavity.

The examination images 12 captured before the insertion of the insertion section 22 are unnecessary for the diagnosis. However, these images are captured at early image capture times, so that they are displayed at the beginning of the chronological order on the display screen 52. Too many unnecessary images cause extra time and trouble to retrieve the at least one examination image 12 that is significant for the diagnosis. By extracting the at least one attached image 12A and displaying the at least one extracted attached image 12A with high priority, the at least one examination image 12 that is significant for the diagnosis is viewed quickly.

Based on the examination report 44, the at least one attached image 12A is extracted. The extracted attached image 12A is the examination image 12 that is significant for the diagnosis. The time and effort for setting a keyword for each of the significant examination images 12 is eliminated. Thus, the at least one examination image 12 that is significant for the diagnosis are viewed easily.

In the case where the examination is performed by the request of the clinician and the examination report 44 is prepared by the endoscopist, the endoscopist finishes the preparation of the examination report 44 before the clinician starts viewing the examination images 12. At the time the clinician views the examination images 12, there is no need for the clinician to prepare the examination report 44. The clinician who requested the examination benefits from the above-described effects and thus it is significantly convenient for the clinician.

As described above, in the entire image display mode illustrated in FIG. 11, the attached images 12A are displayed with high priority by providing the marks 88 to the attached images 12A in the arrangement display area 52B and by selecting the attached image 12A as the top image to be displayed at the top in the switch display area 52A. As illustrated in FIG. 11, the operation buttons 84E and 84F enable switching only among the attached images 12A. Thus, the examination images 12 that are significant for the diagnosis are viewed easily and quickly in the entire image display mode as well as in the report display mode shown in FIG. 10.

The report image display mode, in which only the attached images 12A are displayed, and the entire image display mode, in which all of the examination images 12 including the attached images 12A and the unattached images 12B are displayed, are provided. Thereby the unattached images 12B other than the attached images 12A are viewed easily by switching the mode.

The attached image 12A with the earliest image capture time is selected as the top image. Alternatively, in a case where the attached images 12A include a representative image, the representative image may be selected as the top image. The representative image is a so-called key image, which is the most significant image (e.g. the examination image 12 with the image ID "A13", which is the basis for the findings No. 1 in FIG. 4) among the attached images 12A. The key image is significant for the diagnosis. In a case where the representative image is determined, information for identifying the representative image is attached as the supplementary information to the examination report 44. The attached image extraction unit 94 acquires the image identification information (in this case, the information for identifying the representative image) and identifies the representative image from among the examination images 12 in the image DB 40.

In the report display mode in the above embodiments, the image view support server apparatus 28 acquires the examination images 12 corresponding to the one examination, from the image DB 40. Thereafter, the attached image 12A is extracted in the image view support server apparatus 28. Alternatively, the attached image 12A may be extracted in the image DB 40, without the acquisition of the examination images 12 by the image view support server apparatus 28.

In the above embodiments, the examination ID is inputted to designate (select) the examination. The examination images 12 captured or obtained in the designated examination are displayed on the display screen 52. The present invention is not limited to this. For example, the examination image 12 may be designated (selected) by inputting the image ID to the start screen. The at least one examination image 12 captured or obtained in the same examination as the designated examination image 12 may be displayed on the display screen 52.

The above embodiments describe the two modes: the report image display mode, which is an example of the first display mode, and the entire image display mode, which is an example of the second display mode. Alternatively, the second display mode may be a mode for displaying the at least one attached image 12A and the at least one unattached image 12B. In this case, for example, the attached image 12A and several frames of the unattached images 12B captured immediately before and after the attached image 12A may be selected to be displayed. The rest is eliminated from the display. Thus, the subject to be displayed is limited to the attached image 12A and the unattached images 12B closely correlated with the attached image 12A (e.g. the unattached images 12B captured immediately before and after the attached image 12A). Thereby unnecessary images are efficiently eliminated from the subject to be displayed. In a case where there are a number of unnecessary images, the mode for displaying the at least one attached image 12A and the at least one unattached image 12B is more useful than the entire image display mode because all of the images including the unnecessary images are displayed in the entire image display mode.

On the display screen 52, the examination images 12 are displayed in the chronological order of the image capture time, by way of example. The order of the examination images 12 is not limited to this. For example, the order in displaying or arranging the examination images 12 may be changed to place the two or more attached images 12A close to the top in an order, regardless of the image capture time.

The examination images 12 are not limited to the still images captured at any timing or at predetermined time intervals. The examination image(s) 12 may be one or more frames of the movie. The examination images 12 may include both the still images and the frames of the movie.

Note that, the above embodiments describe a client server type system, in which the display screen 52 is delivered from the image view support server apparatus 28 through the network 34 to the client terminal apparatus 30, by way of example. In this case, the image view support server apparatus 28 is an example of the image view support apparatus. The embodiments are not limited to the client server type system. The client terminal apparatus 30 maybe used as the image view support apparatus. In this case, the CPU 60 of the client terminal apparatus 30 functions as the receiver 90, the image acquisition unit 92, the attached image extraction unit 94, and the screen display controller 96. The receiver 90 receives various operation instructions issued based on the operation of the input device 74 of the client terminal apparatus 30. The screen display controller 96 controls the output of the display screen 52 to the display 72. In the client server type system, the screen display controller 96 controls the output of the display screen 52 from the image view support server apparatus 28 to the client terminal apparatus 30. On the other hand, in the case where the client terminal apparatus 30 is the image view support apparatus, the screen display controller 96 controls the output of the display screen 52 to the display 72.

Various changes and modifications are possible in the present invention and may be understood to be within the present invention.

What is claimed is:

1. An apparatus for supporting viewing a plurality of examination images, the examination images being stored on a per endoscopic examination basis in an image storage unit, the apparatus comprising:
    an endoscope system capturing images;
    a processor configured to extract at least one attached image from the examination images stored in the image storage unit, the attached image being extracted based on an examination report, the examination report being prepared on the per endoscopic examination basis, the at least one of the examination images obtained in the one endoscopic examination being attached to the examination report, the attached image being the examination image attached to the examination report; and
    a screen display controller for performing control to display the extracted attached image on a display screen,
    wherein the examination images include the at least one attached image and at least one unattached image, the unattached image being an examination image not attached to the examination report, and
    the examination images including at least the attached image are displayed in a chronological order of image capture time on the display screen, and
    wherein the apparatus comprises a first display mode, in which only the attached images are displayed in the chronological order on the display screen, and a second display mode, in which the attached images and the at least one unattached image are displayed in the chronological order on the display screen.

2. The apparatus according to claim 1, further comprising an examination designation receiver for receiving designation of the one endoscopic examination from among the endoscopic examinations,
    wherein the processor is configured to extract the at least one attached image from the examination images obtained in the designated endoscopic examination, and
    the screen display controller displays the at least one attached image, out of the examination images obtained in the designated endoscopic examination, on the display screen.

3. The apparatus according to claim 1, wherein the attached image is used as a top image regardless of the image capture time, the top image being displayed at the top in the chronological order on the display screen.

4. The apparatus according to claim 3, wherein, among the attached images, the attached image that is attached as a representative image to the examination report is used as the top image.

5. The apparatus according to claim 1, wherein the display screen comprises a switch display area, in which the examination images are selectively displayed one at a time in the chronological order of the image capture time.

6. The apparatus according to claim 1, wherein the display screen comprises an arrangement display area, in which the examination images arranged in the chronological order of the image capture time are displayed.

7. The apparatus according to claim 1, wherein the examination images stored on the per endoscopic examination basis include still images that are captured automatically at predetermined time intervals.

8. A method for operating an apparatus for supporting viewing a plurality of examination images, the examination images being stored on a per endoscopic examination basis in an image storage unit, the method comprising the steps of:
  capturing at least on endoscopic image;
  extracting at least one attached image from the examination images stored in the image storage unit, the attached image being extracted based on an examination report, the examination report being prepared on the per endoscopic examination basis, the at least one of the examination images obtained in the one endoscopic examination being attached to the examination report, the attached image being the examination image attached to the examination report; and
  performing control to display the extracted attached image on a display screen,
  wherein the examination images include the at least one attached image and at least one unattached image, the unattached image being an examination image not attached to the examination report, and
  the examination images including at least the attached image are displayed in a chronological order of image capture time on the display screen, and
  wherein the apparatus comprises a first display mode, in which only the attached images are displayed in the chronological order on the display screen, and a second display mode, in which the attached images and the at least one unattached image are displayed in the chronological order on the display screen.

9. A non-transitory computer-readable computer medium having instructions stored therein, which, when executed by a computer, cause the computer to perform operations for supporting viewing a plurality of examination images, the examination images being stored on a per endoscopic examination basis in an image storage unit, the operations comprising:
  capturing at least one endoscopic image;
  extracting at least one attached image from the examination images stored in the image storage unit, the attached image being extracted based on an examination report, the examination report being prepared on the per endoscopic examination basis, the at least one of the examination images obtained in the one endoscopic examination being attached to the examination report, the attached image being the examination image attached to the examination report; and
  performing control to display the extracted attached image on a display screen,
  wherein the examination images include the at least one attached image and at least one unattached image, the unattached image being an examination image not attached to the examination report, and
  the examination images including at least the attached image are displayed in a chronological order of image capture time on the display screen, and
  wherein the operations further comprise a first display mode, in which only the attached images are displayed in the chronological order on the display screen, and a second display mode, in which the attached images and the at least one unattached image are displayed in the chronological order on the display screen.

10. The apparatus of claim 1, wherein the processor is configured to extract less than all images attached to an examination report as the attached images, and further configured to extract at least one unattached image from a different examination report.

* * * * *